United States Patent
Young et al.

(10) Patent No.: US 6,971,994 B1
(45) Date of Patent: Dec. 6, 2005

(54) METHOD AND APPARATUS FOR FOCUSSING ULTRASONIC ENERGY

(76) Inventors: Michael John Radley Young, Bremridge House, Bremridge, Ashburton, South Devon (GB) TQ13 7JX; Stephen Michael Radley Young, Bremridge House, Bremridge, Ashburton, South Devon (GB) TQ13 7JX ( * ) Notice: Subject to any disclaimer, the term of this patent is extended or adjusted under 35 U.S.C. 154(b) by 11 days.

(21) Appl. No.: 10/019,295

(22) PCT Filed: Jul. 5, 2000

(86) PCT No.: PCT/GB00/02588

§ 371 (c)(1),
(2), (4) Date: Mar. 22, 2002

(87) PCT Pub. No.: WO01/02055

PCT Pub. Date: Jan. 11, 2002

(30) Foreign Application Priority Data

Jul. 5, 1999 (GB) .................................... 9915707

(51) Int. Cl.$^7$ ............................................. A61N 7/00
(52) U.S. Cl. ........................................................ 601/3
(58) Field of Search ................ 600/439, 459; 601/2–4; 367/150; 73/642, 644; 310/334, 336

(56) References Cited

U.S. PATENT DOCUMENTS

| 3,958,559 | A | * | 5/1976 | Glenn et al. ................. 600/459 |
| 4,858,613 | A | * | 8/1989 | Fry et al. ..................... 600/439 |
| 4,957,099 | A | * | 9/1990 | Hassler ........................... 601/4 |
| 5,036,855 | A |   | 8/1991 | Fry et al. |
| 5,078,144 | A | * | 1/1992 | Sekino et al. ............... 600/439 |
| 5,316,000 | A | * | 5/1994 | Chapelon et al. ........... 600/439 |
| 5,501,655 | A | * | 3/1996 | Rolt et al. ..................... 601/3 |
| 5,507,790 | A |   | 4/1996 | Weiss |
| 5,526,814 | A | * | 6/1996 | Cline et al. ................. 600/411 |
| 5,624,382 | A | * | 4/1997 | Oppelt et al. .................. 601/2 |
| 5,759,162 | A |   | 6/1998 | Oppelt et al. |
| 5,817,021 | A | * | 10/1998 | Reichenberger ............. 600/439 |
| 6,626,854 | B2 | * | 9/2003 | Friedman et al. ............. 601/2 |

FOREIGN PATENT DOCUMENTS

| DE | 37 09 404 | 11/1988 |
| DE | 43 12 264 | 10/1994 |
| WO | 93 19705 | 10/1993 |

* cited by examiner

Primary Examiner—Francis J. Jaworski
(74) Attorney, Agent, or Firm—Carter, DeLuce, Farrell & Schmidt, LLP.

(57) ABSTRACT

An apparatus for treatment of subcutaneous tissue including ultrasonic, e.g. piezoelectric, generators to generate ultrasonic vibrations. Each generator has a lens to focus the ultrasonic vibration at a point within the tissue. The focal point may be moved so that the generated ultrasonic vibrations may be focussed exactly at a point within the tissue that requires treatment. The energy enters the surface of the body over a very wide area, and therefore causes minimum damage to healthy overlying tissue.

14 Claims, 3 Drawing Sheets

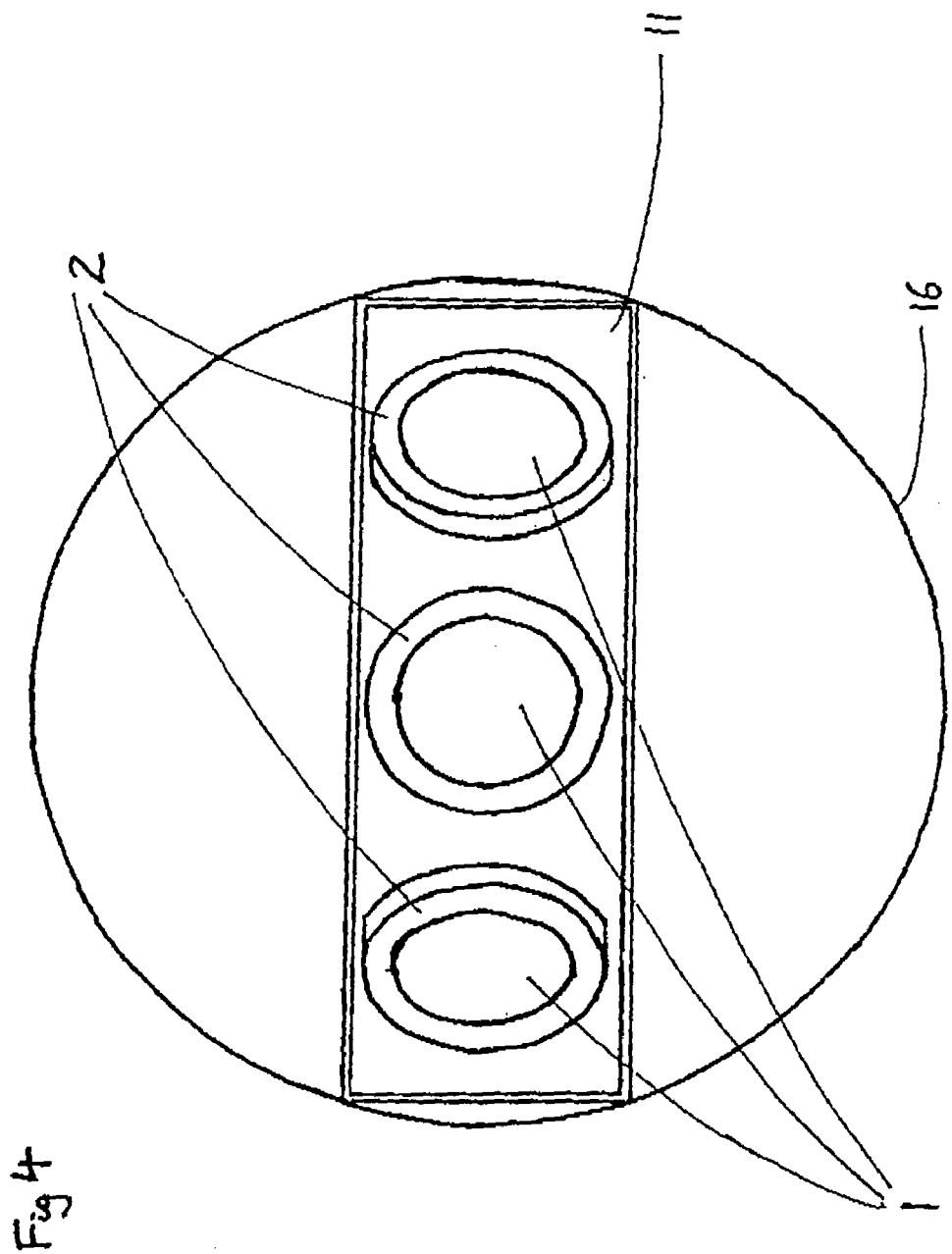

METHOD AND APPARATUS FOR FOCUSSING ULTRASONIC ENERGY

The present invention relates to a method and apparatus for focussing ultrasonic energy. More particularly, but not exclusively, it relates to an apparatus and method for treatment of subcutaneous tissue utilising non-invasive focussed ultrasound.

Tissue which may be treated by the method and apparatus includes subcutaneous blood vessels, unsightly thread veins, selected cancer tissue, and the like. The apparatus may be used for haemostatic cutting and cauterising of blood vessels. It may also be used in other, non-medical, areas where it is desired to apply high intensity energy to a small target zone.

One tissue type which may benefit from such treatment comprises fine arteries and veins lying closely beneath the dermis.

It is well known that fine arteries and veins may become visible in quite random areas closely beneath the dermis. Where these are visible through the dermis in a localised area, these arteries or veins may constitute a serious visual skin blemish.

It is known to remove or treat such blood vessels either using laser energy or by forms of invasive surgery so that the blood supply to that particular part of the vascular system is permanently interrupted and the unsightly blemish may be removed.

However, such known methods of treatment may cause collateral damage to the tissue of the patient being treated or may require lengthy recovery periods.

Similarly, it is well known that certain types of cancerous cell may lie close beneath the surface, such as melanomas or even prostate cancers. Such cancers can sometimes be treated by means of laser irradiation, but there may be damage to surrounding tissue and to the outer layers of the dermis and this may be unacceptable.

It is an object of the present invention to provide a method and apparatus for treatment of subcutaneous tissue which obviates the above disadvantages.

According to a first aspect of the present invention, there is provided an apparatus for treatment of subcutaneous tissue comprising means to generate ultrasonic vibrations, means to focus said ultrasonic vibration at a point within said tissue, and means to move said focal point.

The apparatus may comprise a plurality of generator means to generate ultrasonic vibrations, each being provided with means to focus said ultrasonic vibration at said point within the tissue.

Preferably said means to focus said ultrasonic vibration at said point within tissue comprises lens means.

In the case where there are a plurality of generating means, each may be provided with a respective lens.

The or each lens may be plano-concave.

The or each lens may comprise titanium, titanium alloy, aluminium or an alloy thereof.

The or each lens may be disposed immediately adjacent the respective generator means.

The lens means may be so mounted that the location of the focal point thereof may be moved to impinge directly on the tissue to be treated.

Means to hold the lens means may be movable with respect to the body within which lies the tissue to be treated.

According to a second aspect of the present invention, there is provided a method of treatment of subcutaneous tissue comprising the steps of providing an apparatus as described above, applying said apparatus to a body within which lies the tissue to be treated, and moving said ultrasonic generation means and said focussing means so that their effective distance from to the body within which lies the tissue to be treated is such that the focal point of the lens is coincident with the tissue to be treated.

The tissue to be treated may be subcutaneous blood vessels.

Embodiments of the present invention will now be more particularly described by way of example and with reference to the accompanying drawings, in which:—

FIG. 4 is a plan view of the apparatus of FIG. 3.

Figure 1:
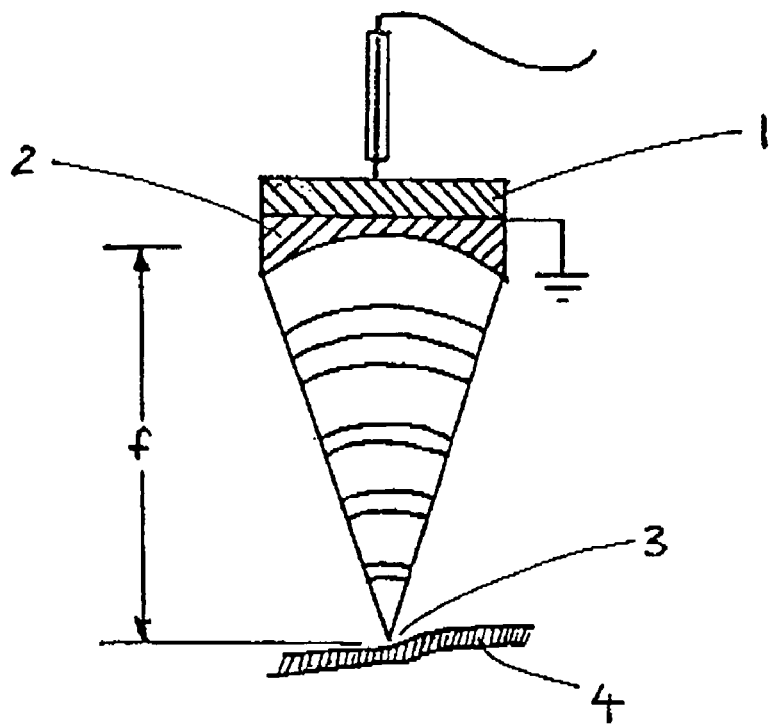
FIG. 1 shows schematically a system for generating high intensity focused ultrasound.
Figure 2:
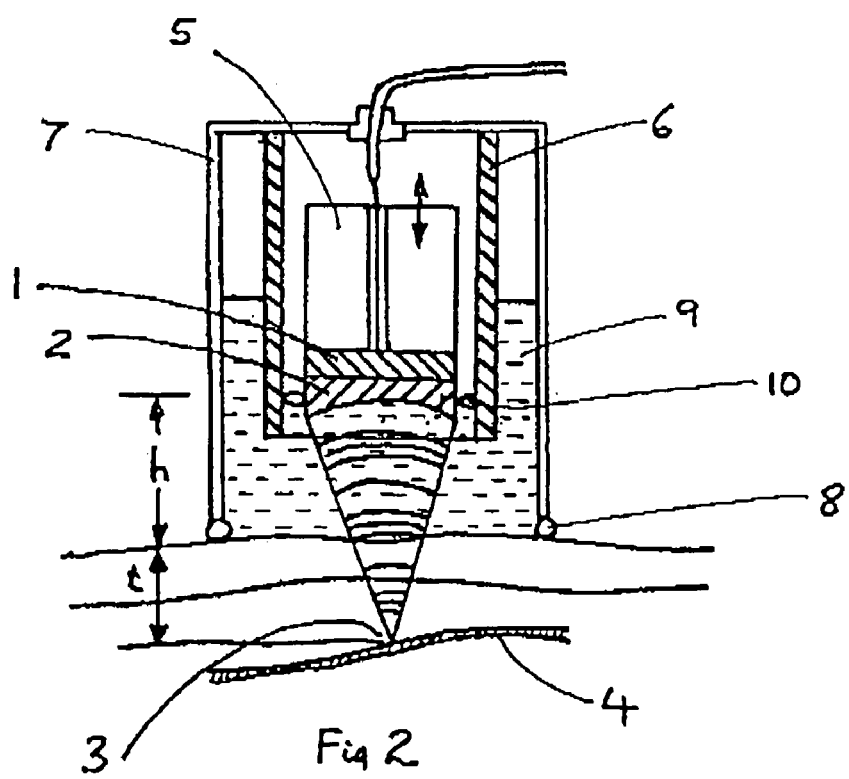
FIG. 2 is a cross-sectional view of an apparatus utilising high intensity focused ultrasound for targeting on to a selected blood vessel.

Referring now to FIGS. 1 and 2 of the drawings, a piezoelectric ceramic disc 1 is adapted to produce high frequency ultrasound in the 1–5 MHz range when excited at an appropriate frequency by electrical means (not shown). Immediately adjacent to the piezoelectric ceramic disc 1 is a focusing plano-concave lens 2 of aluminium alloy or titanium alloy or other suitable material, whereby the ultrasonic vibration is directed to a focal point 3 within the body wherein is located tissue, in this case a blood vessel 4, to be treated.

The focal point 3 may require to be moved to take account of the depth of the blood vessel 4 within the tissue, so that the focal point 3 of the ultrasonic vibration coincides with the vessel 4. This is achieved by moving the assembled piezoelectric disc 1 and lens 2 either towards or away from the surface of the tissue.

Movement is determined according to the formula:

$$f = h + t$$

where f is the focal length of lens 2;

t is the depth of the target tissue 4 beneath the body surface; and h is the height of the lens 2 above the body surface.

Since f is a predetermined constant, for any variation in t, h must be changed.

The assembly of piezoelectric disc 1 and lens 2 is mounted to an inner holder 5 which is itself held to be longitudinally movable with respect to an outer holder 6. A container 7 surrounds the outer holder 6 and is provided with a seal 8 to engage sealingly the body surface. The container 7 is adapted to hold a coupling fluid medium 9, at least filling that part of its volume separating the lens 2 from the body surface. The medium 9 is preferably a gelatinous or aqueous liquid capable of transmitting the ultrasonic vibrations between transmitting bead assembly 1 and 2 and the body surface. A second seal 10 is provided between the relatively movable inner holder 5 and outer holder 6.

As may be seen, use of the invention enables direct absorption of substantially all generated ultrasonic vibrations at a target point within the tissue. This direct absorption of ultrasound in the 1–5 MHz range will cause the temperature of the relatively small volume of the target tissue to rise rapidly, which will cause local coagulation of the vessel 4. Such treatment, when applied over an area of a visual skin blemish, should remove the offending blemishing vessels and improve the appearance of the area.

Figure 3:
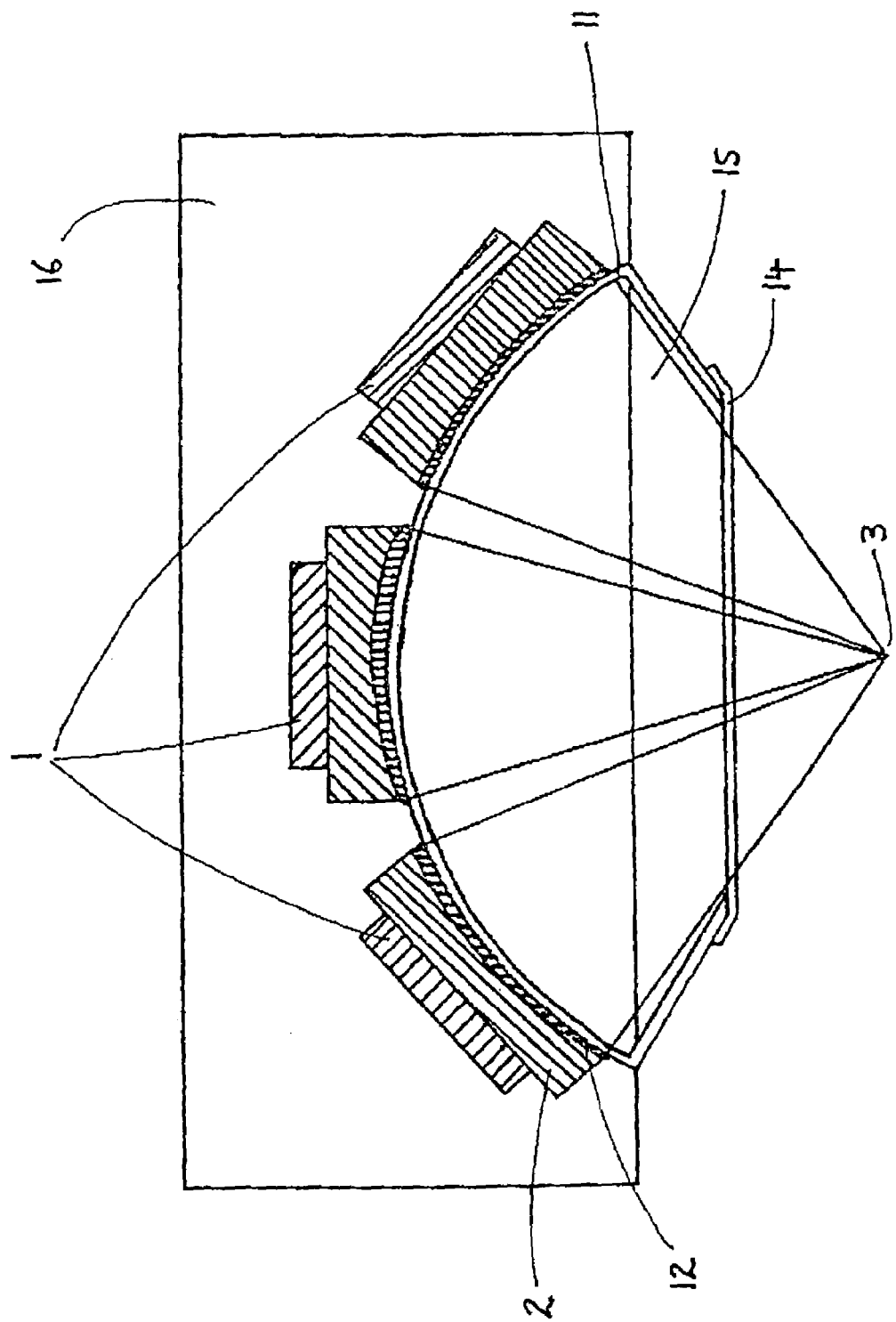
FIG. 3 is a cross-sectional view of an apparatus including three ultrasonic generators.

A further, more powerful, embodiment of the apparatus is shown in FIGS. 3 and 4. In this case, there are provided three ultrasonic generators 1, each associated with a respective piano-concave lens 2. Each of the three generator assemblies is attached by means of a bonding material 12 to a curved mounting plate 11. This mounting plate 11 forms one side of a liquid filled chamber 15, the other side of which is formed by a membrane 14 adapted to contact the surface of the body overlying the target tissue. The membrane 14 is sufficiently flexible to adapt itself to the shape of the body surface and the membrane material has good transmission for ultrasonic vibrations at the frequency (1~5 MHz) being used.

The apparatus including the three generator heads 1 is supported within a container 16 which enables the apparatus to be moved over the surface above the tissue to be treated.

As may be seen, each of the three generators 1 may individually be of comparatively low power intensity, but since all three are focused on the same point 3 within the tissue, the energy at that point 3 is markedly intensified—three times that of the intensity of any one of the individual already focussed beams. As is clear from the Figures, the intensity of the ultrasound at the surface of the body is very low, with any adverse effects minimised because of the wide area within which the beams enter the body. The intensity increases only gradually through the layers of dermis and epidermis to an intensely focus at point 3.

If so desired, more than three generator heads may be used, for example five in a cross configuration, seven in a circular configuration, or any number in any desired arrangement.

The use of the invention has been described by way of a method and apparatus to treat subcutaneous tissue, whether it is blood vessels or cancerous tissue. However, many other uses for the apparatus may be found, and it is not limited to a medical use.

What is claimed is:

1. A non-invasive apparatus for treatment of subcutaneous tissue of a patient, said non-invasive apparatus comprising:
    means for generating ultrasonic vibrations;
    a substantially plano-concave lens disposed immediately adjacent the means for generating ultrasonic vibrations to focus the ultrasonic vibrations at a focal point within the tissue;
    a chamber configured to be positioned on the patient and to at least partially enclose the means for generating ultrasonic vibrations and the substantially plano-concave lens and being uniformly pressurized therein during treatment, wherein the means for generating ultrasonic vibrations includes a plurality of generator means for generating ultrasonic vibrations, wherein each of the plurality of generator means is substantially equally spaced from an adjacent one along a substantially semi-circular plane, and wherein a focal plane of at least one generator means is transverse to a portion of the chamber; and
    means for moving the focal point.

2. An apparatus as claimed in claim 1, wherein each of said plurality of generator means is provided with a respective substantially plano-concave lens disposed immediately thereadjacent to substantially focus the ultrasonic vibrations at said focal point within the tissue.

3. An apparatus as claimed in claim 2, wherein each said respective substantially plano-concave lens is disposed directly adjacent a liquid-filled chamber, adapted to transmit focused ultrasonic vibrations therethrough from each said substantially plano-concave lens to a surface of a body above said subcutaneous tissue to be treated.

4. An apparatus as claimed in claim 1, wherein each of said plurality of generator means is so mounted in fixed relationship to each other generator means that ultrasonic vibrations generated by each generator means are focused at a focal point substantially coincident with the respective focal point of each other generator means.

5. An apparatus as claimed in claim 1, wherein the chamber is a liquid-filled chamber through which ultrasonic vibrations from each generator means may be transmitted to a surface of a body above said subcutaneous tissue to be treated.

6. An apparatus as claimed in claim 1, wherein said substantially plano-concave lens comprises a material selected from the group consisting of titanium, an alloy of titanium, aluminum and an alloy of aluminum.

7. An apparatus as claimed in claim 1, wherein the means for generating ultrasonic vibrations includes at least one piezoelectric member.

8. A non-invasive apparatus for treatment of subcutaneous tissue of a patient, said non-invasive apparatus comprising:
    at least two ultrasonic generators configured to generate ultrasonic vibrations;
    at least one substantially piano-concave lens disposed immediately adjacent the at least two ultrasonic generators to focus the ultrasonic vibrations at a focal point within the tissue;
    a chamber configured to be positioned on the patient and to at least partially enclose the at least two ultrasonic generators and the at least one substantially plano-concave lens and being uniformly pressurized therein during treatment, wherein each of the at least two ultrasonic generators is substantially equally spaced from an adjacent one along a substantially semi-circular plane, and wherein a focal plane of the at least two ultrasonic generators is transverse to a portion of the chamber; and
    a mounting mechanism configured to mount the at least one substantially plano-concave lens and the at least two ultrasonic generators to be moveable together to move the focal point.

9. An apparatus as claimed in claim 8, wherein the at least two ultrasonic generators include a plurality of ultrasonic generators and the at least one substantially plano-concave lens includes a plurality of substantially piano-concave lenses, each of said plurality of substantially plano-concave lenses being disposed immediately adjacent a respective one of the plurality of ultrasonic generators to substantially focus the ultrasonic vibration at said focal point within the tissue.

10. An apparatus as claimed in claim 9, wherein each of said plurality of ultrasonic generators is mounted in fixed relationship to each of the other ultrasonic generators such that its respective substantially plano-concave lens focuses its ultrasonic vibrations at a focal point substantially coincident with said focal point of the respective substantially plano-concave lens of each other ultrasonic generator.

11. An apparatus as claimed in claim 9, the apparatus further comprising a liquid-filled chamber, each of said plurality of substantially plano-concave lenses being disposed directly adjacent said liquid-filled chamber such that ultrasonic vibrations may be passed from each of said substantially plano-concave lenses through said liquid-filled chamber to a surface of a body above the subcutaneous tissue to be treated.

12. An apparatus as claimed in claim 8, wherein the at least one substantially plano-concave lens comprises a material selected from the group consisting of: titanium, an alloy of titanium, aluminum and an alloy of aluminum.

13. A method for treatment of subcutaneous tissue comprising the steps of:
providing an apparatus including at least two ultrasonic generators configured to generate ultrasonic vibrations; at least one substantially plano-concave lens disposed immediately adjacent the at least two ultrasonic generators to focus the ultrasonic vibrations at a focal point within the tissue; a chamber configured to at least partially enclose the at least two ultrasonic generators and the at least one substantially plano-concave lens and being uniformly pressurized therein during treatment, wherein each of the at least two ultrasonic generators are substantially equally spaced from an adjacent one along a substantially semi-circular plane, and wherein a focal plane of the at least two ultrasonic generators is transverse to a portion of the chamber; and a mounting mechanism configured to mount the at least one substantially plano-concave lens and the at least two ultrasonic generators to be moveable together to move the focal point;

applying said apparatus to a body in which lies the tissue to be treated; and moving the at least two ultrasonic generators and the mounting mechanism so that their effective distance from a body surface above the tissue to be treated is such that the focal point of the lens is coincident with the tissue to be treated.

14. A method as claimed in claim 13, wherein the tissue to be treated comprises blood vessels.

* * * * *